US009068927B2

(12) United States Patent
Lee et al.

(10) Patent No.: US 9,068,927 B2
(45) Date of Patent: Jun. 30, 2015

(54) LABORATORY DIFFRACTION-BASED PHASE CONTRAST IMAGING TECHNIQUE (71) Applicant: General Electric Company, Schenectady, NY (US)

(72) Inventors: Susanne Madeline Lee, Cohoes, NY (US); Sudeep Mandal, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 383 days.

(21) Appl. No.: 13/725,480

(22) Filed: Dec. 21, 2012

(65) Prior Publication Data
US 2014/0177801 A1 Jun. 26, 2014

(51) Int. Cl.
| G01N 23/223 | (2006.01) |
| G21K 1/06 | (2006.01) |
| G01N 23/207 | (2006.01) |
| H01J 35/08 | (2006.01) |
| H01J 35/14 | (2006.01) |
| H01J 35/12 | (2006.01) |

(52) U.S. Cl.
CPC ............. *G01N 23/207* (2013.01); *G21K 1/06* (2013.01); *H01J 35/08* (2013.01); *H01J 35/12* (2013.01); *H01J 35/14* (2013.01); *G21K 2207/005* (2013.01); *H01J 2235/086* (2013.01); *H01J 2235/186* (2013.01)

(58) Field of Classification Search
CPC ......... G21K 1/06; G21K 1/065; A61B 6/484; A61B 6/483; A61B 6/542; G01N 23/046; G01N 23/207; G01N 23/201; G01N 23/223; H01J 35/14

USPC ............. 378/84, 62, 71, 70, 82, 86, 138, 143, 378/85, 87, 137, 145, 158, 19, 73; 250/505.1
See application file for complete search history.

(56) References Cited

U.S. PATENT DOCUMENTS

| 6,269,144 | B1 * | 7/2001 | Dube et al. ...................... 378/71 |
| 6,269,145 | B1 * | 7/2001 | Piestrup et al. .................. 378/81 |
| 6,556,652 | B1 * | 4/2003 | Mazor et al. .................... 378/86 |
| 6,577,708 | B2 * | 6/2003 | Chapman et al. ............... 378/82 |
| 6,670,820 | B2 * | 12/2003 | Stokes et al. ............. 324/762.07 |
| 6,947,521 | B2 * | 9/2005 | Wernick et al. ................. 378/70 |
| 7,139,365 | B1 * | 11/2006 | Janik ............................... 378/70 |

(Continued)

OTHER PUBLICATIONS

Kelly, "Phase Contrast Imaging With a Laboratory-Based Microfocus X-Ray Source", Durham University England, pp. 1-249, May 2007.

(Continued)

*Primary Examiner* — David A Vanore
(74) *Attorney, Agent, or Firm* — Robert M. McCarthy (57) ABSTRACT

Embodiments of the disclosure relate to X-ray imaging systems. In one embodiment, the X-ray imaging system features a target configured to receive a focused electron beam from an electron emitter and emit a line source X-ray beam as a result of receiving the focused electron beam; and a monochromator crystal configured to receive the line source X-ray beam from the target and diffract only a portion of the X-rays, wherein the portion of X-rays satisfies the Bragg diffraction condition for the monochromator crystal, and wherein the monochromator crystal is oriented relative to the target such that the portion of the X-rays from the target that satisfy the Bragg condition illuminate an entire length of a surface of the monochromator crystal.

36 Claims, 8 Drawing Sheets

(56) References Cited

U.S. PATENT DOCUMENTS

| | | | |
|---|---|---|---|
| 7,391,850 B2* | 6/2008 | Kaertner et al. | 378/118 |
| 7,394,890 B1* | 7/2008 | Wang et al. | 378/84 |
| 7,505,560 B2* | 3/2009 | Ando et al. | 378/84 |
| 7,555,102 B1 | 6/2009 | Renard-Le Galloudec et al. | |
| 7,693,256 B2 | 4/2010 | Brahme et al. | |
| 7,738,945 B2 | 6/2010 | Fauver et al. | |
| 7,817,777 B2 | 10/2010 | Baumann et al. | |
| 7,817,779 B2* | 10/2010 | Ando | 378/71 |
| 7,889,838 B2 | 2/2011 | David et al. | |
| 8,073,099 B2* | 12/2011 | Niu et al. | 378/36 |
| 8,173,983 B1 | 5/2012 | Sahadevan | |
| 8,204,174 B2* | 6/2012 | Connor et al. | 378/62 |
| 8,208,602 B2 | 6/2012 | Lee et al. | |
| 8,295,443 B2* | 10/2012 | Al-Sadah | 378/143 |
| 8,374,309 B2* | 2/2013 | Donath et al. | 378/19 |
| 2003/0086533 A1* | 5/2003 | Janik et al. | 378/138 |
| 2005/0031073 A1* | 2/2005 | Radley et al. | 378/47 |
| 2007/0069125 A1* | 3/2007 | Schueler et al. | 250/305 |
| 2007/0291896 A1* | 12/2007 | Parham et al. | 378/37 |
| 2009/0092227 A1* | 4/2009 | David et al. | 378/36 |
| 2009/0129551 A1* | 5/2009 | Butler et al. | 378/143 |
| 2012/0039438 A1* | 2/2012 | Parham et al. | 378/62 |
| 2012/0188556 A1* | 7/2012 | Nagai | 356/521 |
| 2014/0064445 A1* | 3/2014 | Adler | 378/43 |
| 2014/0177801 A1* | 6/2014 | Lee et al. | 378/73 |

OTHER PUBLICATIONS

Herzen, "A Grating Interferometer for Materials Science Imaging At a Second-Generation Synchrotron Radiation Source", Zur Erlangung des Doktorgrades des Department Physik der Universität Hamburg, pp. 1-108, 2010.

* cited by examiner

LABORATORY DIFFRACTION-BASED PHASE CONTRAST IMAGING TECHNIQUE

BACKGROUND

The subject matter disclosed herein relates to x-ray imaging techniques and, in particular, to diffraction-based phase contrasting imaging techniques with laboratory-based X-ray sources.

In non-invasive imaging systems, X-ray tubes are used in various X-ray systems and computed tomography (CT) systems as a source of X-ray radiation. The radiation is emitted in response to control signals during an examination or imaging sequence. Typically, the X-ray tube includes a cathode and an anode. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce X-ray radiation to be emitted toward an imaged volume.

Conventional X-ray imaging systems may detect an imaged volume based on absorption of the X-ray radiation. However, absorption-based techniques may provide images with insufficient distinction between certain types of tissue structures. For example, tumors and fluid-filled cysts may be difficult to distinguish on images generated by X-ray absorption of tissue. Other techniques, such as diffraction-based phase contrast techniques, may provide images with more contrast between different types of tissue structures. However, such techniques generally involve X-ray sources with relatively high flux, such as synchrotron sources, which are not widely available.

BRIEF DESCRIPTION

In one embodiment, an X-ray imaging system is provided. The X-ray imaging system includes an x-ray source wherein an X-ray target is configured to receive a focused electron beam having a cross sectional shape that is rectangular, with an aspect ratio of at least 50:1, from an electron emitter and emit a line source X-ray beam as a result of receiving the focused electron beam; and a monochromator crystal configured to receive the line source X-ray beam from the target and diffract a portion of the X-rays, wherein the portion of X-rays that are diffracted satisfies the Bragg condition for the monochromator crystal, and wherein the monochromator crystal is oriented relative to the X-ray target such that the portion of the X-rays from the target that satisfy the Bragg condition illuminate a defined area of a surface of the monochromator crystal.

In another embodiment, a phase contrast imaging system is provided. The phase contrast imaging system includes an X-ray source, the X-ray source comprising: an emitter configured to emit an electron beam; one or more focusing elements configured to focus the electron beam into a rectangular cross-sectional shape; a target configured to receive the focused electron beam and emit an X-ray beam as a result of receiving the focused electron beam, wherein an impact area of the focused electron beam is a line having an aspect ratio of at least 50:1; and a monochromator crystal configured to receive the X-ray beam from the target and diffract only a portion of the X-rays, and wherein the monochromator crystal is oriented relative to the target such that the X-rays diffracted by the monochromator crystal illuminate an entire region of interest of a sample; an X-ray detector configured to detect X-rays transmitted through the region of interest and generate a signal based on the detected X-rays; and data acquisition circuitry configured to convert the signal generated by the detector into one or more phase contrast images of the region of interest.

In yet another embodiment, a method of X-ray imaging is provided. The method includes the steps of emitting an electron beam having a cross-section having a major axis and a minor axis; contacting a target with the electron beam; generating an X-ray beam as a result of contact of the electron beam on the target, wherein the electron beam impacts the target in an area having an aspect ratio of the major axis to the minor axis of at least 50:1; contacting a monochromator crystal with the X-ray beam with the monochromator crystal configured to diffract only the X-rays of the X-ray beam that satisfy the Bragg condition for the monochromator crystal, wherein the monochromator crystal is oriented relative to the target such that the X-rays that satisfy the Bragg condition illuminate an entire dimension of the monochromator crystal; and detecting the diffracted X-rays that are transmitted through an object of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Provided herein are X-ray imaging systems that are capable of being used for phase contrast imaging, X-ray dark-field imaging, or other X-ray diffraction-enhanced imaging techniques that employ high brilliance X-ray beams. In one embodiment, the techniques incorporate a line focus X-ray beam that is oriented relative to a monochromator crystal (or other suitable diffracting element) such that the X-rays that satisfy the Bragg condition have sufficient flux for phase contrast and/or absorption imaging. The techniques may incorporate a target that includes structural features that result in improved heat dissipation and faster cooling in the target. Such improved cooling in turn can permit greater electron beam power deposition into the target, which can result in increased X-ray production. For line-focus electron beam shapes, such structural features may yield X-ray flux densities that approach (e.g., is within an order of magnitude) that of synchrotron sources. In one embodiment, an x-ray beam generated by the disclosed techniques has energies within a range of approximately 10 keV to approximately 100 keV. In a particular embodiment, the x-ray beam generated by the disclosed techniques has energies of at least 18 keV or at least 60 keV. For example, higher energies maybe appropriate for industrial inspection, while lower energies may be appropriate for medical imaging. However, it should be understood that the techniques and X-ray systems disclosed herein may be used for any desired application.

The disclosed techniques provide a laboratory-based X-ray source for high resolution diffraction-based techniques. Because synchrotron sources are hugely costly and available at a limited number of locations, laboratory-based X-ray sources improve access and costs for performing phase contrast imaging.

The X-ray imaging systems disclosed herein may be used in conjunction with any suitable type of x-ray imaging. The operating environment of the disclosure is described with respect to a diffraction-based phase contrast imaging system. In addition, the present techniques are equally applicable to other X-ray based systems, including fluoroscopy, absorption-based x-ray imaging, such as mammography, angiography, and standard radiographic imaging systems, as well as radiation therapy treatment systems and sample analysis such as x-ray diffraction and fluorescence systems.

Figure 1:
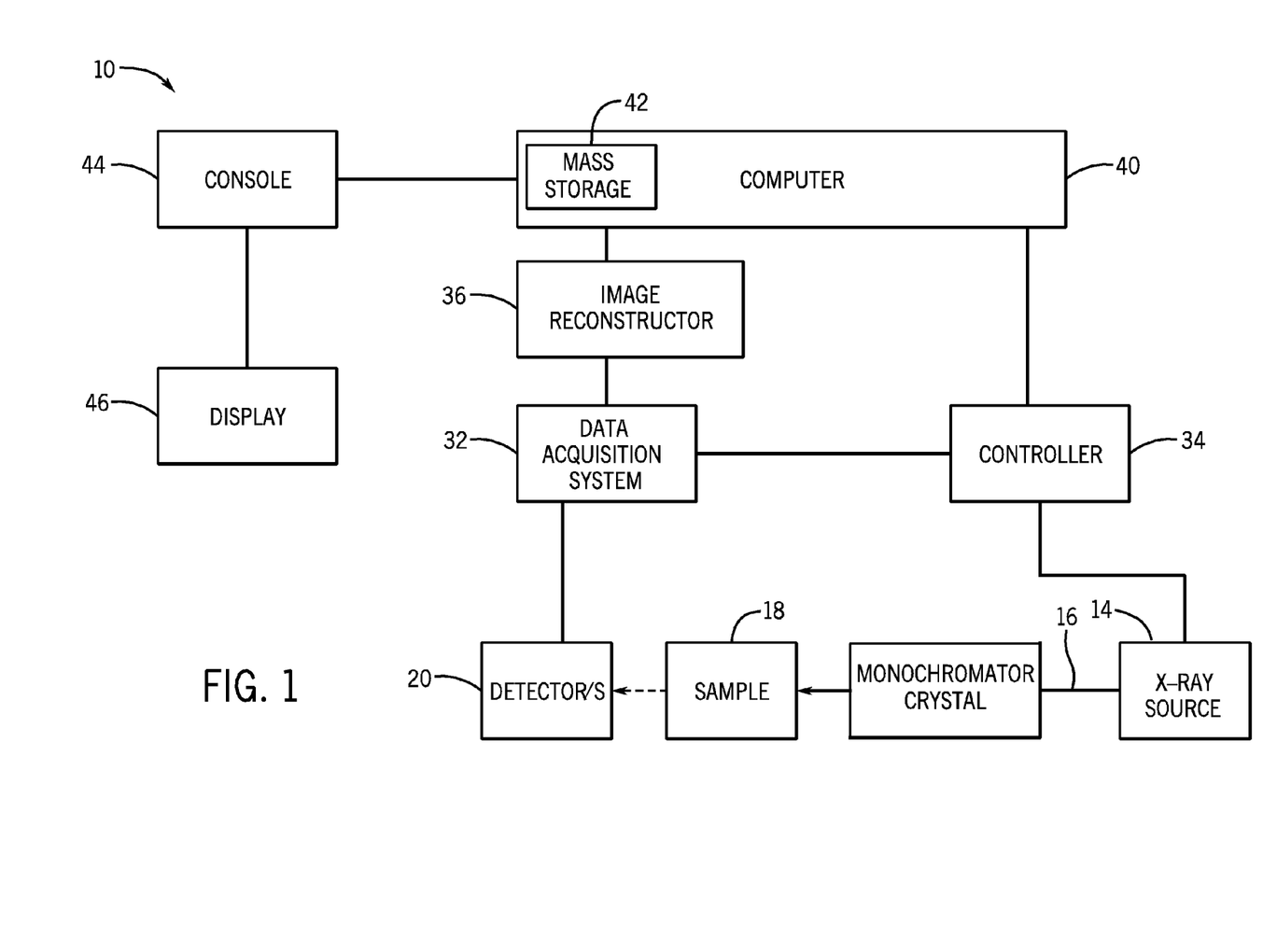
FIG. 1 is a block diagram of an X-ray imaging system incorporating an embodiment of the present disclosure.

Referring to FIG. 1, an X-ray imaging system 10 is shown as including an X-ray source 14 that projects a beam of X-rays 16 through a monochromator crystal (see FIG. 6) and a patient and/or sample 18 toward one or more detector 20. The detector 20 is coupled to a data acquisition system 32. The one or more detectors 20 sense the transmitted X-rays that pass through the sample 18, and the data acquisition system 32 converts the sensed X rays to digital signals for subsequent processing. Each detector 20 produces an electrical signal that represents the intensity of an impinging X-ray beam after it passes through the sample 18. The operation of the X-ray source 14 may be governed by an X-ray controller 34 that provides power and timing signals to the X-ray source 14. An image reconstructor 36 receives sampled and digitized X-ray data from the data acquisition system 32 and performs reconstructions to produce absorption and/or phase contrast images. The reconstructed image is applied as an input to a processor-based computer 40 that stores the image in a mass storage device 42.

The computer 40 also receives commands and scanning parameters from an operator via a console 44 that has some form of operator interface, such as a keyboard, mouse, voice activated controller, or any other suitable input apparatus. An associated display 46 allows the operator to observe the reconstructed images and other data from the computer 40. The operator-supplied commands and parameters are used by the computer 40 to provide control signals and information to the data acquisition system 32 and the X-ray controller 34.

Figure 2:
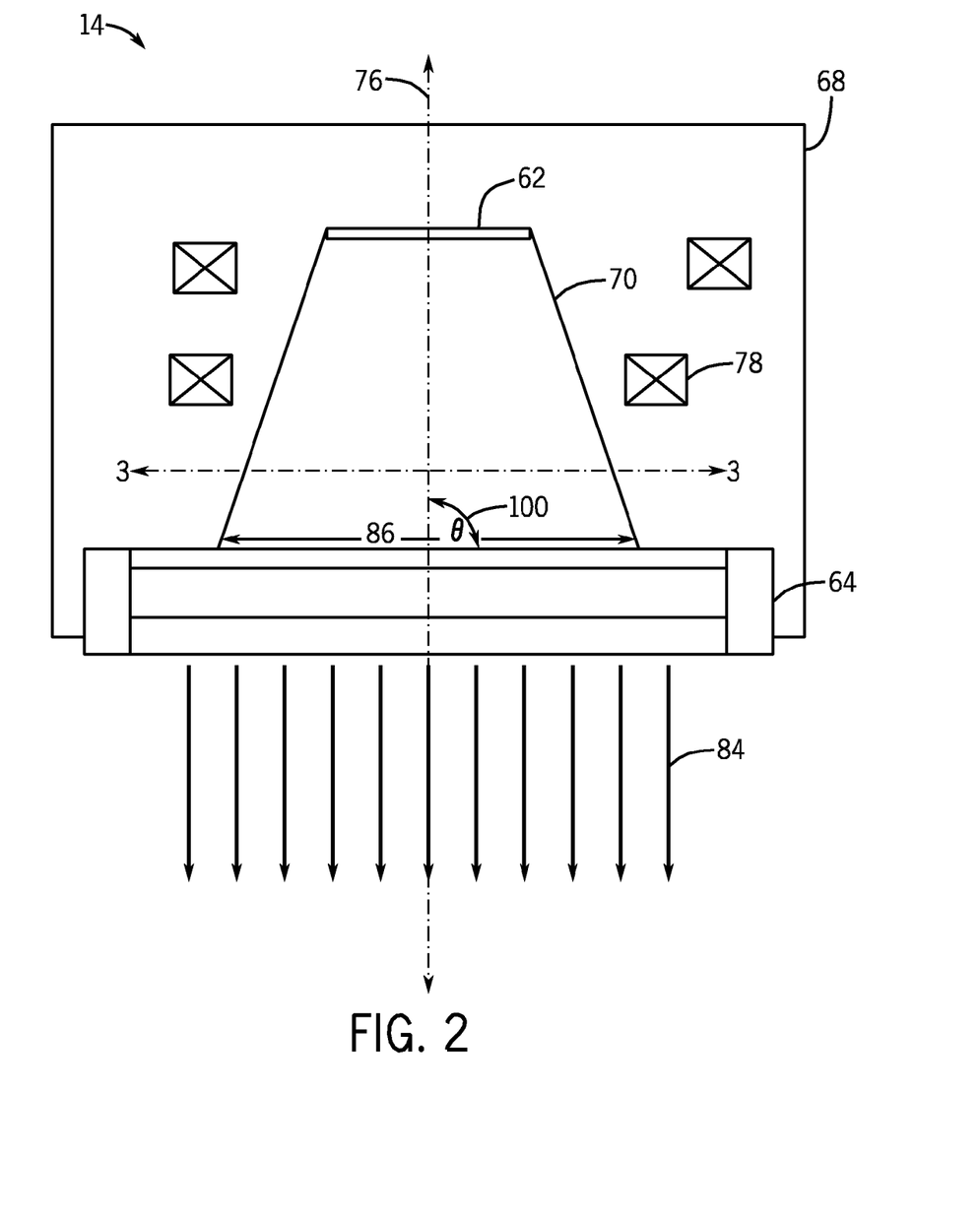
FIG. 2 is a front view of the X-ray source of the system illustrated in FIG. 1.
Figure 3:
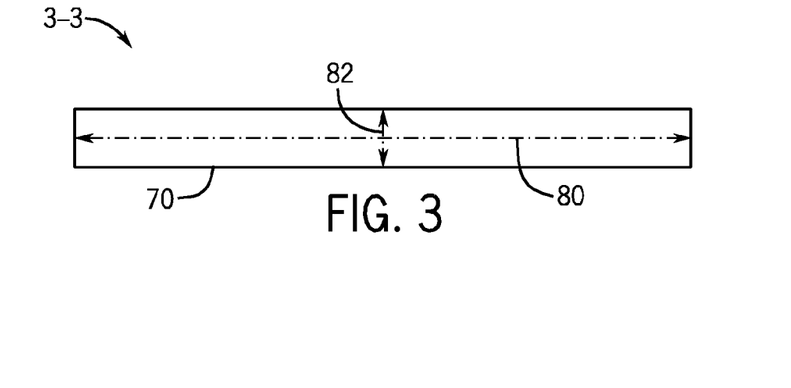
FIG. 3 is a cross-section of the electron beam near its focus shown in FIG. 2.

Referring now to FIG. 2, the X-ray source 14 included in the system 10 (FIG. 1) is shown in a front view. The X-ray source 14 includes an electron emitter 62 and a target 64 within a housing 68 defining an area of relatively low pressure (e.g., a vacuum). The electron emitter 62 may be any suitable type, including for example thermionic and/or cold cathode emitters, or pyroelectric crystals for generating a shaped electron beam 70. In one embodiment, the emitter 62 is a wire; in another embodiment, the emitter 62 may be V-shaped. In particular, as opposed to sources that use an electron beam that is generally circular in cross-section, the present techniques incorporate an electron emitter 62 that emits an electron beam with a particular aspect ratio or having a particular shape, e.g., taken as a cross-section of the beam 70 at a section 3-3 orthogonal to an axis 76 of electron flow or at a point of impact with the target 64. For example, the emitter 62 may emit an electron beam 70 having a rectangle shape, a line shape, or an elliptical shape. The general shape of the electron beam 70 may be focused with one or more optics 78 which may include features (e.g., inductive coils) configured to shape the beam 70 using one or more electro-magnetic fields. In essence, these electro-magnetic fields serve to shape and steer the electron beam 70.

FIG. 3 is an example of a cross-section of a generally rectangular beam at or parallel to section 3-3. In one embodiment, the cross-sectional shape of the electron beam 70 has a longer dimension along a major axis 80 and a shorter dimension along a minor axis 82. It should be understood that the dimensions of the cross-sectional shape may change along the axis 76 of electron flow.

Figure 4:
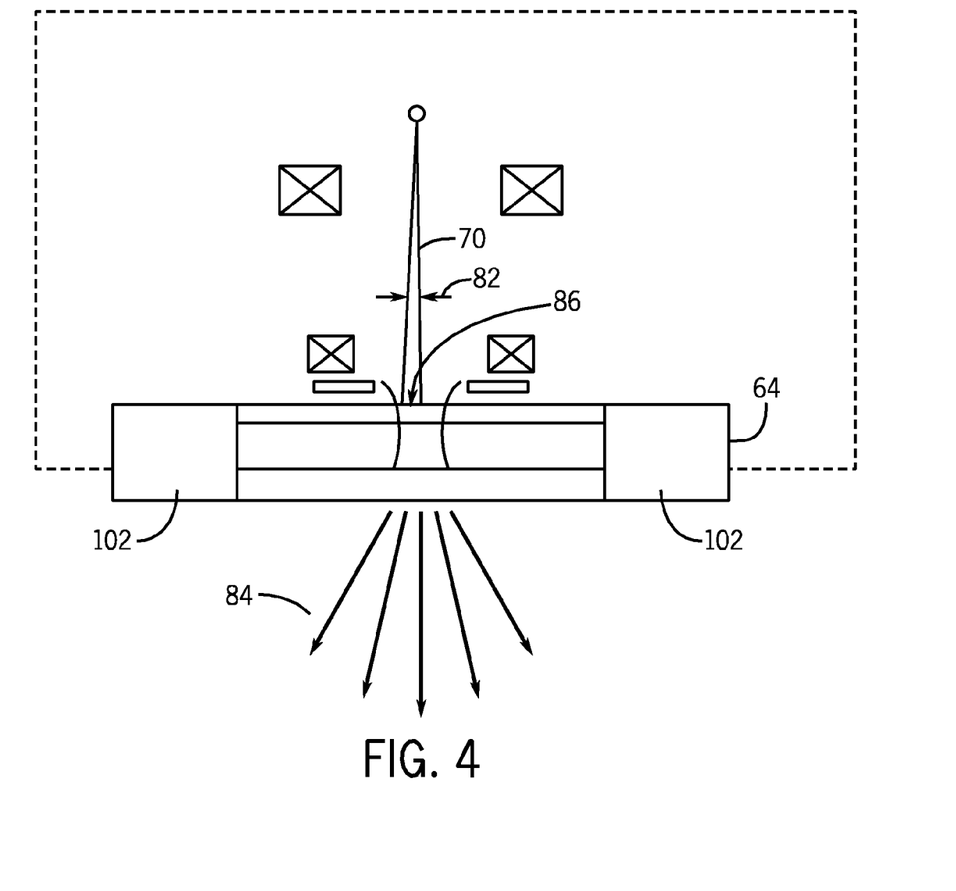
FIG. 4 is a side view of the X-ray source of FIG. 2.

Turning back to FIG. 2, when struck by an electron beam 70, the target 64 emits an X-ray beam 84. The electron beam 70 impacts the target 64 on an impact surface 86 and on a portion of the target defining a focal spot. The focal spot may have a particular shape, thickness, or aspect ratio to achieve particular characteristics of the emitted X-ray beam 84. FIG. 4 is a side view of the X-ray source 14 of FIG. 2 showing a minor axis 82 of the electron beam 70. As shown in this side view, the X-ray beam 84 fans out from the target 64.

That is, the emitted X-ray beam 84, while having a fan-shape, is produced by a line source of electrons 70, i.e., an electron beam having a line shape defined by a particular line thickness or a particular aspect ratio. In certain embodiments, the electron beam 70 at the impact area 86 on the target 64 may be characterized by a particular aspect ratio or ratio of a major axis 80 to a minor axis 82, e.g., at least 100:1, 200:1, 500:1, 750:1 or 1000:1 at a point of impact or impingement. Furthermore, the aspect ratio may be between 200:1 and 5000:1, between 500:1 and 2500:1, or between 750:1 and 1250:1 at a point of impact or impingement. The impact area 86 on the target 64 may also be characterized by a thickness dimension of a line. For example, the line thickness of a line source (e.g., the size of the electron beam 70) at the impact area 86 may be less than 50, 20, 10, 5, 3, 1, or 0.5 microns. This thickness may determine the resolution of the imaging system. By way of a non-limiting example, at the impact area 86, the minor axis 82 may be approximately 10 microns in size, and the major axis 80 may be approximately 1 centimeter in size.

As noted, while the depicted embodiments show a transmission-type arrangement (e.g., with the X-ray beam emitted from an opposing surface of the target) of the electron transmitter and the target, the techniques provided herein may also be implemented in a reflectance-type arrangement. Further, the electron flow axis 76 forms an angle 100 (see FIG. 2) relative to the impact surface 86 of the target 64. The angle 100 may be 90 degrees, i.e., may be orthogonal. In other embodiments, the electron beam axis may form an acute angle with the impact surface of the target. In such embodiments, the cross sectional shape of the electron beam 70 may be characterized at the impact surface 86 or at a section generally orthogonal to the electron beam axis 76. In the case of a non-orthogonal electron beam axis, the target material through which the electrons travel may be made thinner, because the oblique electron path may result in greater electron absorption than in the orthogonal case. In addition, such arrangements may be associated with lower X-ray flux density.

The target 64 may be manufactured of any metal or composite, such as tungsten, molybdenum, copper, or any material that contributes to Bremsstrahlung (i.e., deceleration) radiation when bombarded with electrons. Further, as provided herein, the material from which the target is formed may include heat dissipating, heat spreading, or microstructural features that contribute to a relatively higher flux density for the resultant X-ray beam. These features may be formed on or in the target 64 and/or may be included as one or more layers of the target 64. In this manner, improved heat dissipation and heat spreading may yield X-ray beams of high brilliance with a stationary (e.g., non-rotating) target 64.

Further, in one embodiment, the thermal energy conducted away from impact area 86 may be directed towards one or more cooling jackets 102 configured to circulate a cooling fluid (e.g., water, ethylene glycol) about at least a portion of the target 64. The cooling fluid may be provided by a cooling system, which is configured to provide active cooling of the source 14 and, more specifically, the target 64. The operation of the cooling system may be controlled, at least in part, by the controller 26. For example, during the course of operation, the cooling system may adjust the flow of the cooling fluid through the jacket 102 in response to variations in the electron beam 70, such as variations in the flux of the beam 70.

The target 64 may also include a via or channel that defines an impact area 86 and that may have any suitable geometry, including any suitable size and/or shape. In certain embodiments, the particular geometry of the via or channel may depend on the size and/or shape of the electron beam 70 and, more specifically, on the geometry of the electron beam impact area 86. For example, in embodiments where the electron beam 70 has an extreme aspect ratio (e.g., between 200:1 and 5000:1 as noted above) and is rectangular in shape, the via or channel may have a similar shape. That is, the via or channel may be a rectangular channel similar in shape to the geometry provided in FIG. 3. Additionally or alternatively, the size of the channel may be substantially the same size or larger than the electron beam impact area 86.

Figure 5:
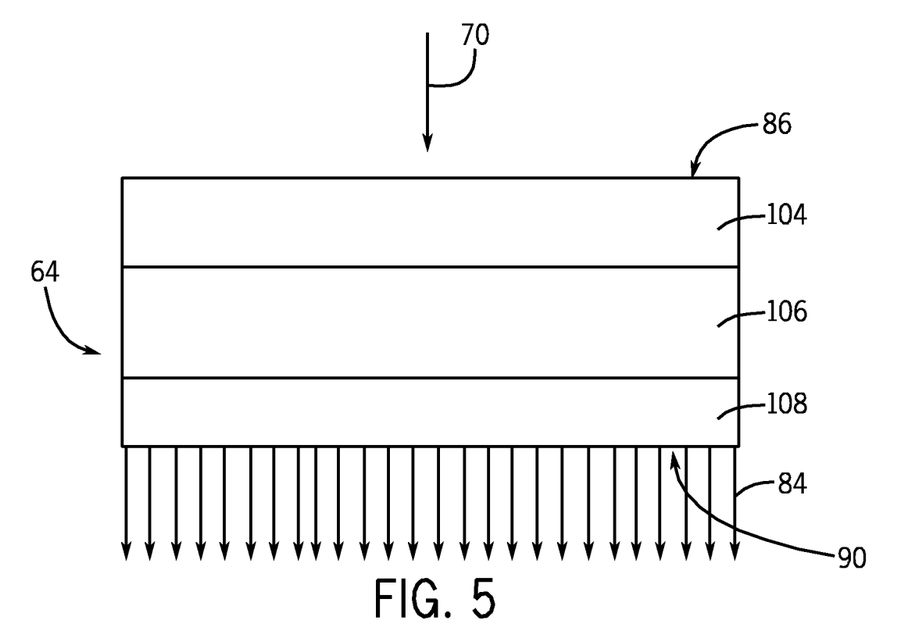
FIG. 5 is a side view of a multilayer target that may be used in conjunction with the X-ray source illustrated in FIG. 2.

In the embodiment illustrated in FIG. 5, the source target 64 may include a top heat spreading layer 104, which is first impinged by the electron beam 70, a target layer 106, which produces the majority of X-rays 84 emitted by the source 14 when impinged by the electron beam 70, and, in certain embodiments, an X-ray window 108 out of which the X-rays 84 are emitted. In other embodiments, the target 64 may include more or fewer layers, depending upon the particular implementation. In a general sense, the configuration of the multilayer source target enables thermal conductance away from an impact area 86 of the target 64. In particular embodiments, a top heat spreading layer 104 may be used with or without a via or channel microstructure formed into the target layer 106.

In certain embodiments, the emitted X-ray beam 84 has characteristics that are related to the size and shape of the focal spot on the target 64. Accordingly, the X-ray beam 84 exits the target 64 from an X-ray emission area determined by the focal spot. The emitted X-ray beam 84 may be shaped by additional features, including any window 108 disposed on or that is part of the X-ray emission surface 90 (e.g., on an opposing surface 90 of the target 64). The shape and composition of the window 108 may prevent a portion of the emitted X-rays from being exiting the source 14. In addition, the X-ray source 14 may also include one or more beam shaping features (e.g., apertures or slits) that are spaced apart from the target 64 and that, at least in part, define a shaped of the emitted X-ray beam 84. The window and beam shaping features may be used together or separately.

As noted above, the target 64 may have a plurality of layers including at least a top heat spreader 104, the target layer 106, and a window 108, though other layers may also be included, as discussed below. As generally noted above, the thermal conductivity of the target 64 may enable the electron beam 70 to be directed at the target 64 in a substantially continuous manner, rather than in a time-pulsed mode. Further, the thermal conductivity of the target 64 may also enable an increase in the density of the electron beam 70 without detrimentally affecting the target 64. Indeed, heat dissipating materials, heat spreading materials, or other microstructural features may be included in the design of the target 64, which collectively enable a relatively higher flux density for the resultant X-ray beam 84.

The top heat spreader 104 (e.g., a first layer) may include one or more materials (e.g., one or more first materials) that impart a higher overall thermal conductivity to the heat spreader than the target layer, which may include any metal or composite, such as tungsten, molybdenum-rhodium, copper, or any other material that produces Bremsstrahlung (i.e., deceleration or braking) radiation when bombarded with electrons. In addition, the top heat spreader 104 may have a higher overall melting point than the target layer 106. Generally, the top heat spreading layer 104 is configured to conduct heat in a direction away from the electron impact area 86 (FIG. 4), such as laterally away. The top heat spreading layer 104 may have a relatively high lateral thermal conductivity, i.e., conductivity in a direction approximately parallel to the shorter dimension of the thermal produced by the electron beam on the target, have a relatively high thickness conductivity, i.e., conductivity in a direction substantially aligned with the axis 76 (FIG. 2), or both. In accordance with present embodiments, the overall lateral and/or thickness thermal conductivity of the top heat spreading layer 104 (and other heat spreading layers disclosed herein) may be higher than the overall corresponding thermal conductivity of the target layer 106. By way of non-limiting example, the top heat spreading layer 104 may include carbon-based materials including but not limited to highly ordered pyrolytic graphite (HOPG), diamond, amorphous carbon, diamond-like carbon (DLC), or the like, and/or metal-based materials such as beryllium oxide, silicon carbide, silicon nitride, copper-molybdenum, oxygen-free high thermal conductivity copper (OFHC), or any combination thereof. Hybrid materials such as alumina-diamond may also be used. In some embodiments, the top heat spreading layer 104 may include HOPG, diamond, or a combination thereof, and the target layer 106 may include tungsten. Example heat spreading materials that may be incorporated into any one or a combination of the heat spreading layers disclosed herein are provided in Table 1 below, which provides the electrical nature of each material, along with composition, thermal conductivity, coefficient of thermal expansion (CTE), density, and melting point.

TABLE 1

Example Heat Spreader Materials

| Material | Function | Electrical | Composition | Thermal Conductivity W/m-K | CTE ppm/K | Density g/cm³ | Melting point °C. |
|---|---|---|---|---|---|---|---|
| Diamond | Heat spreader | Insulator | Polycrystalline diamond | 1200 | 1.5 | 3.5 | 3550 |
| Beryllium oxide | Heat spreader | Insulator | BeO | 250 | 7.5 | 2.9 | 2578 |
| CVD SiC | Heat spreader | Insulator | SiC | 250 | 2.4 | 3.2 | 2830 |
| Aluminum nitride | Heat spreader | Insulator | AlN | 170 | 4.3 | 3.3 | 2200 |
| Alumina | sub amount | Insulator | $Al_2O_3$ | 30 | 7.3 | 3.9 | 2072 |
| Cu—Mo | Heat spreader | Conductor | Cu—Mo | 400 | 7 | 9-10 | 1100 |
| Ag-Diamond | Heat spreader | Conductor | Ag-Diamond | 650 | <6 | 6-6.2 | 961-3550 |
| AlSiC | Heat spreader | Conductor | AlSiC | 180 | 6.5-9 | 3 | 600 |
| OFHC | Heat spreader | Conductor | Cu | 390 | 17 | 8.9 | 1350 |

In embodiments where the X-ray source 14 is a transmission X-ray source, the X-ray window 108 (FIG. 5) may be a part of the target 64, or may be in thermal communication with the target 64. In the illustrated embodiment, the X-ray window 108 is in thermal communication with the target layer 106. In accordance with present embodiments, the X-ray window 108 may have a relatively high thickness thermal conductivity (i.e., aligned with the axis 76) to enable the X-ray window 108 to dissipate or otherwise conduct thermal energy to its outer perimeter, where heat rejection via air convection or a forced cooling system may be facilitated. The X-ray window 108 may have a higher overall thermal conductivity than the target layer 106, and a melting point that is at most equal to or lower than the melting point of the target layer 106. By way of non-limiting example, the window 108 may be diamond or beryllium.

It should be noted that the target 64 may include as little as one layer, but is not limited to a particular number of layers. For example, in certain embodiments, the target layer 106 may act as the X-ray window 108 (FIG. 5) by separating the vacuum space (FIG. 2) from the ambient environment around the X-ray source 14, and by serving as the window through which X-rays are emitted. Similarly, in some embodiments, the target 64 may only include the top heat spreader 104 (FIG. 5) and the X-ray target layer 106. The target may also include one or more heat spreading layers in addition to the top heat spreader 104.

The target 64 may be fabricated using any suitable technique, including chemical vapor deposition (CVD), sputtering, layer-by-layer assembly, and so on. However, due to the variance in materials utilized to achieve the particular thermal conductivity desired for the target 64, certain transition materials may be utilized between each layer to minimize the thermal and mechanical disparity between the layers. For example, carbon-based materials may be thermally conductive via phonon travel (i.e., elastic vibrations in the material's lattice), while metallic materials may be thermally conductive via the metal's loosely bound valence electrons. These dissimilar modes of thermal conductance can sometimes severely impede the thermal conductance between layers. In addition, materials having dissimilar coefficients of thermal expansion can delaminate from each other when exposed to high temperatures. Accordingly, in such situations, it may be desirable to provide a transition material that prevents thermal resistance between the layers of the target 64 while also allowing thermal expansion at elevated temperatures.

Figure 6:
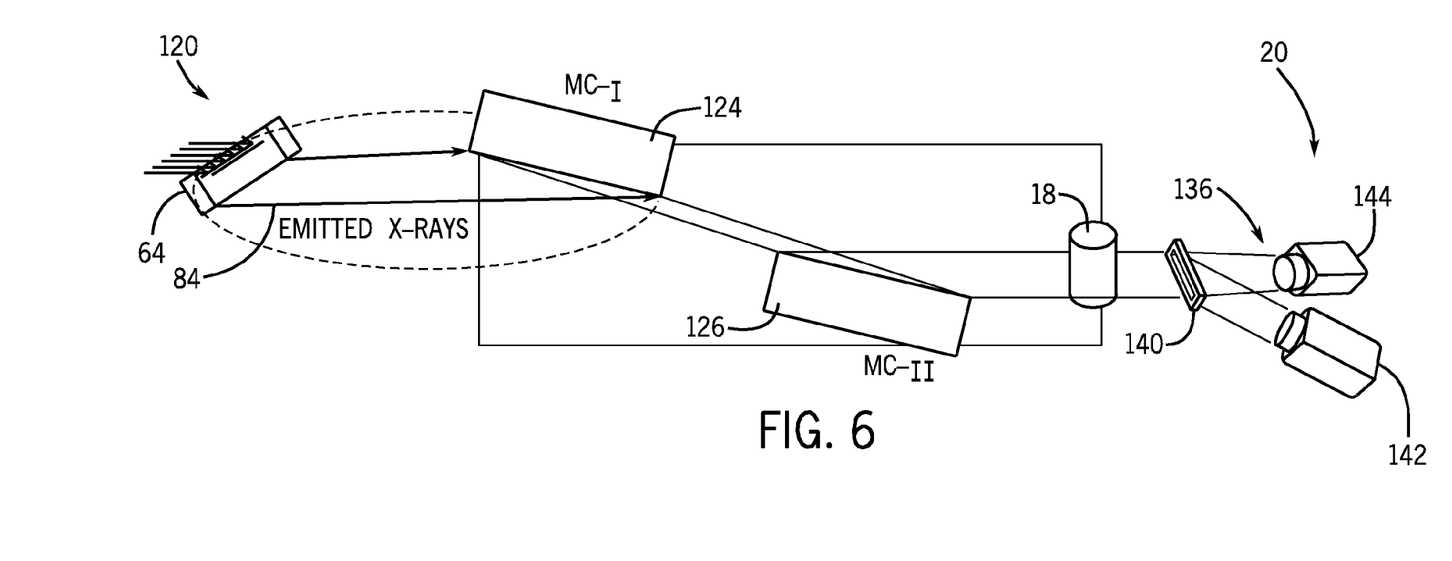
FIG. 6 is a schematic view of a diffraction-based phase contrast imaging system incorporating an embodiment of the present disclosure.

As noted, the X-ray source 14 may be used in conjunction with a diffraction-based phase contrast imaging system. For example, such a system 120 is shown in FIG. 6. The system uses an x-ray beam 84 generated from the target 64 to detect an image of an object. In the depicted embodiment, the x-ray source 14 is a line x-ray source, such as those shown in FIG. 2. The x-ray beam 84 is diffracted by a crystal monochromator 124. In another embodiment, one or more second monochromator crystals 126 may be used to increase the monochromaticity and decrease the divergence of the x-ray beam before it impinges on the sample. The diffracted X-rays that satisfy the Bragg condition for the monochromator crystal 124 pass through the sample 18 and to the analyzer system 136 that includes an angle analyzer 140, which may be a Bragg type crystal analyzer. The analyzer system 136 also includes one or more detectors 20. Any suitable detector may be used. In the depicted embodiment, the analyzer system includes an x-ray detector 20 that detects the intensity $I_T$ of X rays undeflected and therefore transmitted straight through the sample 18. These X rays satisfy the Bragg condition for diffraction by the Angle Analyzer crystal and are redirected by the LAA to the x-ray detector 20, where an absorption image is generated. The system also includes an x-ray detector 144 that detects only those X rays that have been refracted by the sample. These X rays pass through the LAA undeflected and with minimal intensity loss due to the concept of anomalous diffraction. In this manner, the system 120 is a capable of acquiring both absorption and diffraction-enhanced images.

With regard to the monochromator crystals (e.g., monochromator crystals 124 or 126) used in conjunction with the system 120, these crystals are capable of diffracting those incident X-rays that satisfy the Bragg condition for diffraction, i.e. those X rays that are incident on the crystals at a Bragg angle for that crystal. In particular, a given X-ray beam 84 is polychromatic and includes X-rays at a number of wavelengths and angles. The monochromator only diffracts those wavelengths that obey Bragg's law λ=2d sin θ for particular d spacings of the crystal, which are related to the interatomic spacings within the crystal. In one embodiment, a monochromator crystal 124 may be tuned to a characteristic wavelength (i.e., X-ray fluorescence) of the target 64.

Figure 7:
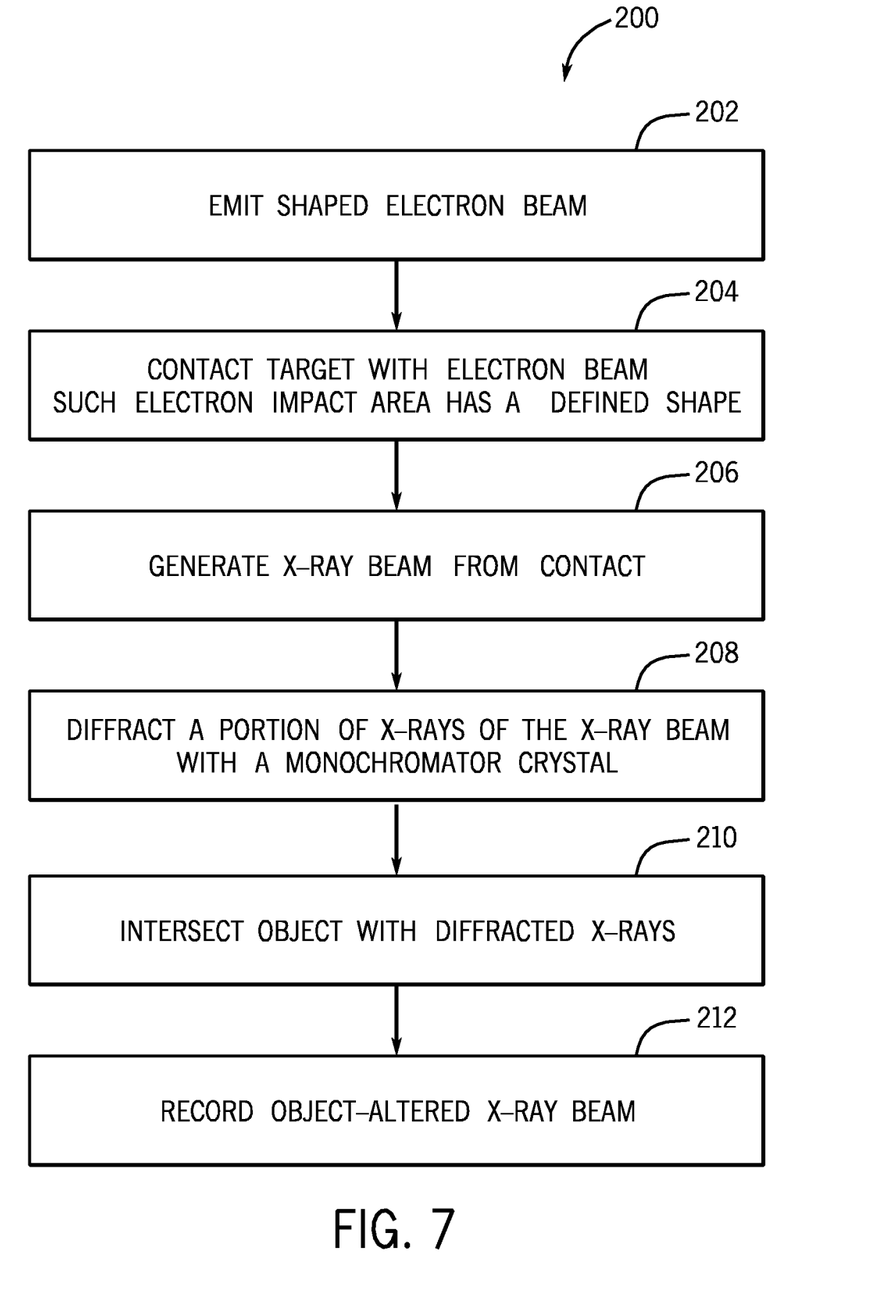
FIG. 7 is a flow diagram of a method for producing the X-ray beam of a diffraction-based phase contrast imaging incorporating an embodiment of the present disclosure.

The techniques provided herein can also be used in imaging methods. FIG. 7 is a flow diagram 200 of a method that includes the step of emitting an electron beam having a desired shape at block 202. In certain embodiments, the emitted electron beam may be generally linear or rectangular. In other embodiments, the emitted electron beam is noncircular or asymmetric about one or more axes. Further, the emitted electron beam may be further focused via one or more electron optics to compress one or more of the electron beam dimensions. The emitted electron beam contacts a target at block 204. In certain embodiments, the emitted electron beam at the electron impact area on the target may be characterized by a shape having a particular aspect ratio, e.g., at least 500:1 or by a thickness dimension of a line. For example, the line thickness of a line source may be less than 50 microns.

As a result of interactions between the electron beam and the target atoms as the electron beam travels through the target, an X-ray beam is generated at block 206. The X-ray beam then contacts a monochromator crystal at block 208. The monochromator crystal diffracts only the X-rays of the correct energy and angle to satisfy the Bragg condition for diffraction. In one embodiment, the monochromator crystal is oriented relative to the target such that the X-rays that satisfy the Bragg condition illuminate an entire length of a surface of the monochromator crystal. In other embodiments, the arrangement between the target and the monochromator crystal is selected based on the monochromator crystal diffracting plane orientation, the X-ray energy of the imaging system application, and the materials from which the monochromator crystal is formed. The X-rays diffracted by the monochromator crystal then intersect an object at block 210 to be imaged or analyzed, where multiple effects can alter the X-ray intensity and/or direction, e.g. absorption, scattering, diffraction, fluorescence, and/or refraction. The sample-altered X-ray beam can be then be recorded at block 212 with, for example, a digital x-ray imaging detector.

Figure 8:
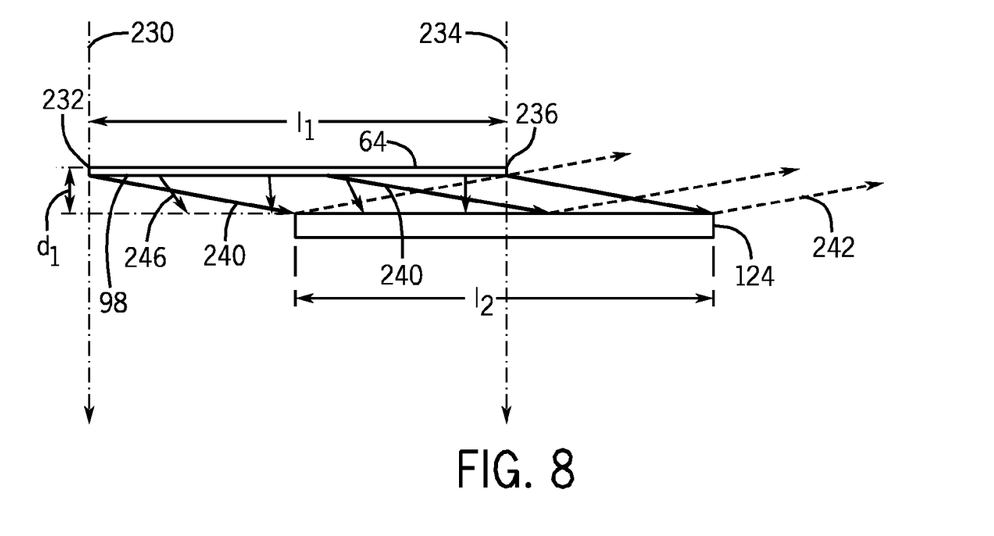
FIG. 8 is a diagrammatical front view of an X-ray target orientation that can produce X-rays capable of illuminating an entire surface of a monochromator crystal parallel to the target incorporating an embodiment of the present disclosure.

The arrangement of the target relative to the monochromator crystal 124 may be selected to maximize the brilliance of the X-ray beam on the sample. As noted above, the monochromator crystal can only diffract X-rays of a particular energy that intersect the monochromator crystal atomic planes at the Bragg angle for diffraction. Accordingly, in FIGS. 8 and 9, the X-ray emission area 98 of the target 64 may be oriented relative to the monochromator crystal 124 so that the X-rays that are diffracted by the monochromator crystal 124 illuminate an entire dimension of the monochromator crystal 124. The entire dimension may be a length of the crystal 124 or may be an entire dimension along an asymmetric surface of a nonparallel crystal plane, as discussed. In the example shown in FIG. 8, the X-ray emission area 98 of the target 64 is parallel to the monochromator crystal 124. The X-ray emission area 98 has a length $l_1$ that is about equal to a length $l_2$ of the monochromator crystal. The X-ray emission area 98 of the target 64 is spaced apart from the monochromator crystal 124. In addition, the X-ray emission area 98 is parallel to and offset from the monochromator crystal 124 to account for the Bragg angle. That is, an orthogonal axis 230 through a first end 232 of the X-ray emission area 98 does not intersect the monochromator crystal 124 while a second orthogonal axis 234 through a second end 236 of the X-ray emission area 98 intersects the monochromator crystal 124. Further, the distance $d_1$ between the target 64 and the monochromator crystal 124 may be selected to maximize the desired X-ray brilliance with this geometry of source and monochromator. In certain embodiments, a closer spacing may be advantageous. In one embodiment, the distance $d_1$ may be expressed as:

$$d_1 = (l_2)\left[\frac{\tan(\vartheta_{Bragg})}{2}\right]$$

In another embodiment, the distance $d_1$ may be expressed differently if the monochromator crystal is cut asymmetrically, i.e. the crystal planes are not parallel to the top surface of the crystal, so as to expand the x-ray beam for increased sample coverage. In that case, $$d_1 = (l_2)\left[\frac{\tan(\vartheta_{Bragg} + \vartheta_{Asymmetric\,cut}) \times \tan(\vartheta_{Bragg} - \vartheta_{Asymmetric\,cut})}{\tan(\vartheta_{Bragg} + \vartheta_{Asymmetric\,cut}) + \tan(\vartheta_{Bragg} - \vartheta_{Asymmetric\,cut})}\right]$$

To maximize the x-ray beam intensity exiting the monochromator, all of the X-rays, represented by arrows 240, that can be diffracted by the monochromator crystal 124, should be diffracted, represented by arrows 242. Other X-rays, represented by arrows 246, that do not satisfy to the Bragg condition for the monochromator crystal 124, are not diffracted. To maximize the amount of diffracted X-rays, the length $l_1$ of the X-ray emission area 98 may be selected such that an entire length $l_2$ of the monochromator crystal 124 is illuminated by X rays 240 that satisfy the Bragg condition. In other embodiments, the illuminated dimension may be selected based on the orientation of the atomic planes of the monochromator crystal 124, as given by the second formula above.

Figure 9:
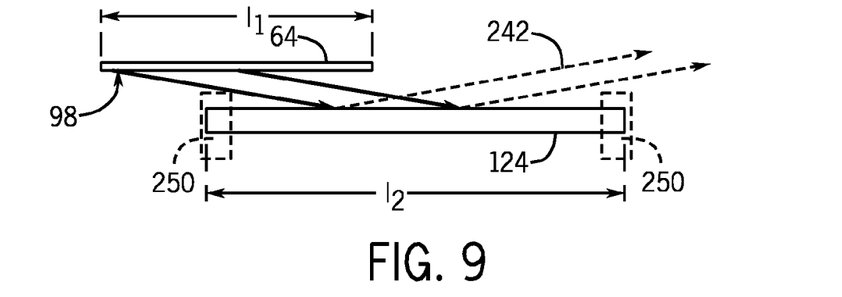
FIG. 9 is a diagrammatical front view of an X-ray target that can produce X-rays capable of illuminating only part of a surface of a monochromator crystal parallel to the target incorporating an embodiment of the present disclosure.
Figure 10:
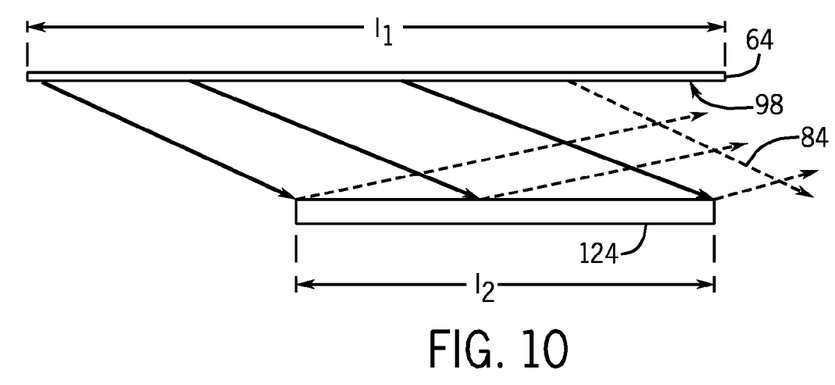
FIG. 10 is a diagrammatical front view of an X-ray target that can produce X-rays capable of illuminating an entire surface of a monochromator crystal parallel to the target from a longer separation distance incorporating an embodiment of the present disclosure.

In other embodiments, as shown in FIG. 9, the length $l_1$ of the X-ray emission area 98 may be selected to avoid certain areas (e.g., ends 250) of the monochromator crystal 124 or to illuminate a defined area on the monochromator crystal 124. Such an embodiment may be advantageous if the monochromator crystal 124 includes known stress points or irregularities. In the depicted embodiment, the length $l_1$ of the X-ray emission area 98 is shorter than the active dimension, e.g., the length $l_2$, of the monochromator crystal 124. Accordingly, the ends 250 are not illuminated by X-rays that satisfy the Bragg condition. In an alternate embodiment, shown in FIG. 10, the X-ray emission area 98 is longer than the monochromator crystal 124, which may be desirable if the x-ray beam has non-uniformities that should not be diffracted by the monochromator 124. In the depicted embodiment, while the entire length $l_2$ (and active dimension) of the monochromator crystal 124 is illuminated, the X-ray beam 84 also illuminates areas past the monochromator crystal 124.

Figure 11:
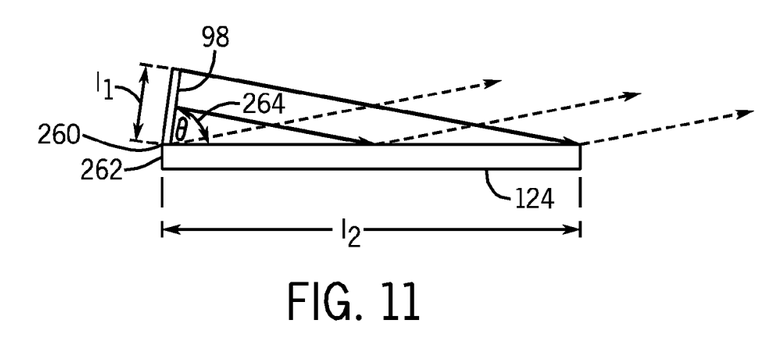
FIG. 11 is a diagrammatical front view of an X-ray target that can produce X-rays capable of illuminating an entire surface of and forms an acute angle with a monochromator crystal incorporating an embodiment of the present disclosure.

While certain embodiments of the disclosure relate to a parallel orientation of the target 64 with respect to the monochromator crystal 124, the system 120 may also encompass other arrangements. For example, as shown in FIG. 11, the X-ray emission area 98 may be positioned at an angle with the monochromator crystal 124. In such an embodiment, an end 260 of the X-ray emission area 98 may be positioned adjacent to an end 262 of the monochromator crystal 124 to form an angle 264. In such an embodiment, the length $l_1$ of the X-Ray emission area 98 may be adjusted to account for the closer distance between these components. In the extreme embodiment in which the angle 264 is 90 degrees, the general formula for determining the length $l_1$:

$$l_1 = l_2 \times \sin(\theta_{Bragg})$$

In asymmetrically cut monochromator crystals, the top surface of the crystal 124 is typically only a few tenths of a degree different from the Bragg angle, i.e. the angle between the top surface of the monochromator crystal 124 and the atomic diffracting planes in the crystal is almost but not quite the Bragg angle for diffraction. This difference may be expressed as: $(\theta_{Bragg} - \theta_{Asymmetric\ cut}) \sim$ few tenths of a degree. The length $l_1$ of the X-Ray emission area 98 that produces the maximal x-ray flux on the monochromator crystal for the nearly perpendicular geometry is:

$$l_1 = l_2 \times \sin(\theta_{Bragg} - \theta_{Asymmetric\ cut})$$

Figure 12:
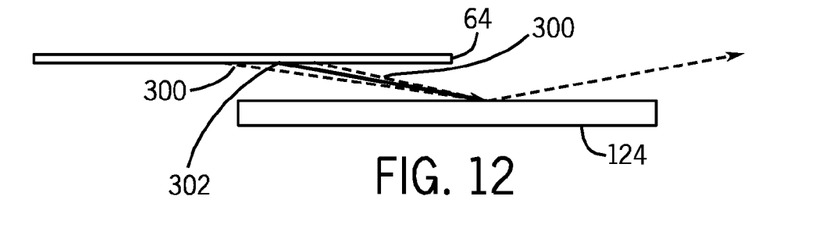
FIG. 12 is a diagrammatical front view of X-rays within a numerical aperture for diffraction from a monochromator crystal parallel to the target incorporating an embodiment of the present disclosure.
Figure 13:
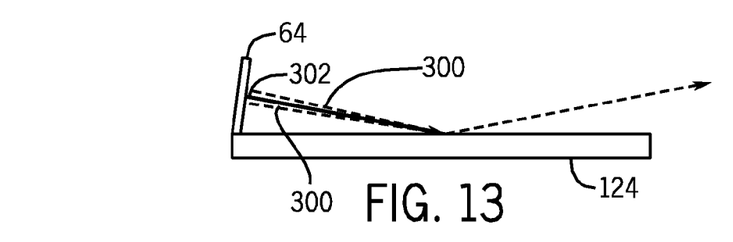
FIG. 13 is a diagrammatical front view of X-rays within a numerical aperture for diffraction from an angled monochromator crystal incorporating an embodiment of the present disclosure.

Regardless of the arrangement of the target 64 relative to the monochromator crystal 124, the X-rays that satisfy the Bragg condition generally fall within a numerical aperture of the monochromator crystal 124. That is, a particular monochromator crystal 124 can diffract X rays within a tolerance or numerical aperture of the Bragg diffraction angle. In other words, X rays with energies slightly less than or slightly greater than those satisfying the Bragg diffraction condition will also be diffracted by the monochromator crystal. The size of this numerical aperture may influence the resultant X-ray brilliance. For example, stress and strain in the monochromator crystal may give rise to a large numerical aperture, but at the cost of greater divergence in the diffracted x-ray beam and thus lower X-ray flux density at the sample. In the geometry where the target 64 is parallel to the monochromator crystal 124, the numerical aperture for diffraction 300 is depicted in FIG. 12 and shows that a larger area 302 produces X rays that can satisfy the diffraction condition than in the angled or perpendicular orientations (see FIG. 13). In this manner, the parallel geometry may compensate for a relatively larger average distance travelled (i.e., path length to the monochromator crystal 124) for the X-rays, which in turn results in reduced brilliance ($1/R^2$ intensity as a function of the path length). The reduced brilliance therefore may be overcome in part by the increased X-ray generation area via the numerical aperture. Alternatively, the angled orientation, shown in FIG. 13, includes a smaller X-ray production area 302 within the numerical aperture, but is associated with a shorter path length.

It should be understood that a diffraction-based X-ray phase contrast imaging system may be configured to select a desired X-ray brilliance by taking into account the diffracting plane of a particular monochromator crystal 124, the numerical aperture of the monochromator crystal 124, the X-ray energy for the desired application, and the materials from which the target 64 and the monochromator crystal 124 are formed. For example, the orientation of the target 64 relative to the monochromator crystal 124 may be parallel or at an angle. Further, the particular angle may also be selected to achieve a desired X-ray brilliance. In one particular embodiment, the X-ray brilliance achieved is within an order of magnitude of synchrotron-based sources and may be at least $10^{11}$ ph/s/mm$^2$/mrad$^2$/0.25% bw.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
    an x-ray source wherein an X-ray target is configured to receive a focused electron beam having a cross-sectional shape that is rectangular, with an aspect ratio of at least 50:1, from an electron emitter and emit a line source X-ray beam as a result of receiving the focused electron beam; and
    a monochromator crystal configured to receive the line source X-ray beam from the target and diffract a portion of the X-rays, wherein the portion of X-rays that are diffracted satisfies the Bragg condition for the monochromator crystal, and wherein the monochromator crystal is oriented relative to the X-ray target such that the portion of the X-rays from the target that satisfy the Bragg condition illuminate a defined area of a surface of the monochromator crystal.

2. The X-ray imaging system of claim 1, wherein the target comprises:
    a first layer comprising a first material; and
    a second layer in thermal communication with the first layer and comprising a second material; and
    wherein the first layer is positioned closer to the electron emitter than the second layer, and the first material has a higher thermal conductivity than the second material.

3. The X-ray imaging system of claim 2, wherein the second layer is a target layer having an electron beam impact area at which the focused electron beam impacts the target layer, and the first layer comprises a via or channel corresponding to the electron beam impact area.

4. The X-ray imaging system of claim 1, wherein the portion of X-rays that satisfy the Bragg diffraction condition for the monochromator crystal are at the characteristic fluorescence radiation energy for the target.

5. The X-ray imaging system of claim 1, wherein the target comprises an area that receives the focused electron beam having an aspect ratio of at least 1000:1.

6. The X-ray imaging system of claim 1, wherein the target comprises an area that receives the focused electron beam having a minor axis that is 50 microns or less.

7. The X-ray imaging system of claim 1, wherein the target comprises an area that receives the focused electron beam having a first dimension that is in a range of 0.1 mm to 100 mm and a second dimension that is in a range of 0.1 to 100 microns.

8. The X-ray imaging system of claim 1, wherein the target comprises an area that receives the focused electron beam having a longest dimension that is the same or longer than a longest dimension of a surface of the monochromator crystal.

9. The X-ray imaging system of claim 1, wherein the target comprises an area that receives the focused electron beam having a longest dimension that is shorter than a longest dimension of a surface of the monochromator crystal.

10. The X-ray imaging system of claim 1, wherein the direction of propagation of the focused electron beam is orthogonal to a surface of the target.

11. The X-ray imaging system of claim 1, wherein the target comprises a first material and a second material adjacent to the first material in a transmission arrangement wherein X rays are emitted from a volume in the second material.

12. The X-ray imaging system of claim 1, wherein the target is parallel to the monochromator crystal.

13. The X-ray imaging system of claim 12, wherein the target comprises a volume with a cross-sectional area that receives the focused electron beam, wherein said cross-sectional area only partially overlaps the monochromator crystal such that an orthogonal axis through a non-overlapping end of the electron beam target area does not intersect a diffracting portion of the monochromator crystal.

14. The X-ray imaging system of claim 12, wherein the target is spaced apart from the monochromator crystal a distance that is a function of the length of the monochromator crystal and the Bragg angle for the monochromator crystal, and the angle the diffracting Bragg planes make with the top surface of the monochromator crystal.

15. The X-ray imaging system of claim 1, wherein the target and the monochromator crystal form an acute angle.

16. The X-ray imaging system of claim 1, comprising a window that defines an X-ray emission area on the target.

17. The X-ray imaging system of claim 1, wherein the defined area is less than a length of the monochromator crystal.

18. The X-ray imaging system of claim 1, comprising a beam-shaping element attached to the target or spaced apart from the target.

19. The X-ray imaging system of claim 1, comprising one or more (?) second monochromator crystals configured to diffract the portion of X-rays from the source.

20. The X-ray imaging system of claim 1, comprising an angle analyzer.

21. The X-ray imaging system of claim 1, comprising an absorption-based image acquisition element and a phase contrast image acquisition element.

22. The X-ray imaging system of claim 1, wherein the target is stationary.

23. A phase contrast X-ray imaging system, comprising:
an X-ray source, the X-ray source comprising:
an emitter configured to emit an electron beam
one or more focusing elements configured to focus the electron beam into a rectangular cross-sectional shape;
a target configured to receive the focused electron beam and emit an X-ray beam as a result of receiving the focused electron beam, wherein an impact area of the focused electron beam is a line having an aspect ratio of at least 50:1; and
a monochromator crystal configured to receive the X-ray beam from the target and diffract only a portion of the X-rays, and wherein the monochromator crystal is oriented relative to the target such that the X-rays diffracted by the monochromator crystal illuminate an entire region of interest of a sample;
an X-ray detector configured to detect X-rays transmitted through the region of interest and generate a signal based on the detected X-rays; and
data acquisition circuitry configured to convert the signal generated by the detector into one or more phase contrast images of the region of interest.

24. The phase contrast X-ray imaging system of claim 23, wherein the target comprises a plurality of layers having different thermal properties.

25. The phase contrast X-ray imaging system of claim 23, wherein the target comprises one or more microstructures defining the impact area of the focused electron beam.

26. The phase contrast X-ray imaging system of claim 23, wherein the X-ray beam emitted from the X-ray source has a brilliance of at least $10^{11}$ ph/s/mm$^2$/mrad$^2$/0.25% bw.

27. The phase contrast X-ray imaging system of claim 23, wherein target and the monochromator crystal are in a transmission configuration.

28. The phase contrast X-ray imaging system of claim 23, wherein the X-ray source is a transmission source.

29. The phase contrast X-ray imaging system of claim 23, wherein the region of interest is a portion of the sample.

30. The phase contrast X-ray imaging system of claim 23, comprising an angle analyzer configured to reflect or transmit the diffracted X-rays to the region of interest.

31. A method of X-ray imaging, comprising:
emitting an electron beam having a cross-section having a major axis and a minor axis;
contacting a target with the electron beam;
generating an X-ray beam as a result of contact of the electron beam on the target, wherein the electron beam impacts the target in an area having an aspect ratio of the major axis to the minor axis of at least 50:1;
contacting a monochromator crystal with the X-ray beam with the monochromator crystal configured to diffract only the X-rays of the X-ray beam that satisfy the Bragg condition for the monochromator crystal, wherein the monochromator crystal is oriented relative to the target such that the X-rays that satisfy the Bragg condition illuminate an entire dimension of the monochromator crystal; and
detecting the diffracted X-rays that are transmitted through an object of interest.

32. The method of claim 31, comprising focusing the electron beam into a line.

33. The method of claim 31, where the electron beam has a rectangular cross section.

34. The method of claim 31, comprising emitting the X-ray beam through a window coupled to the target, wherein the window defines a shape of the emitted X-ray beam.

35. The method of claim 31, wherein contacting the target with the electron beam comprises contacting one or more microstructures formed in the target.

36. The method of claim 31, wherein contacting the target with the electron beam comprises contacting one or more layers formed in the target with different respective thermal conductivities.

* * * * *